(12) United States Patent
Sander

(10) Patent No.: US 7,387,385 B2
(45) Date of Patent: Jun. 17, 2008

(54) SURGICAL MICROSCOPE

(75) Inventor: Ulrich Sander, Rebstein (CH)

(73) Assignee: Leica Microsystems (Schweiz) AG, Heerbrugg (CH)

(*) Notice: Subject to any disclaimer, the term of this patent is extended or adjusted under 35 U.S.C. 154(b) by 544 days.

(21) Appl. No.: 10/761,064

(22) Filed: Jan. 20, 2004

(65) Prior Publication Data
US 2004/0156017 A1 Aug. 12, 2004

(30) Foreign Application Priority Data
Jan. 21, 2003 (DE) ............... 103 02 401

(51) Int. Cl.
*A61B 3/14* (2006.01)
*A61B 3/10* (2006.01)

(52) U.S. Cl. .................. 351/206; 351/216

(58) Field of Classification Search ............... 351/205, 351/206, 216, 217, 221; 359/656–661; 348/78–80
See application file for complete search history.

(56) References Cited

U.S. PATENT DOCUMENTS

| 5,116,116 A * | 5/1992 | Aizu et al. ............ 351/221 |
| 5,535,060 A | 7/1996 | Grinblat |
| 5,865,829 A | 2/1999 | Kitajima |
| 5,907,431 A * | 5/1999 | Stuttler ............ 359/379 |
| 6,212,006 B1 | 4/2001 | Reiner |
| 6,267,752 B1 | 7/2001 | Svetliza |
| 6,309,070 B1 | 10/2001 | Svetliza et al. |
| 6,309,080 B1 | 10/2001 | Svetliza et al. |
| 6,685,317 B2 * | 2/2004 | Su et al. ............ 351/206 |
| 6,921,169 B2 * | 7/2005 | Su et al. ............ 351/206 |

FOREIGN PATENT DOCUMENTS

WO WO0227379 4/2002

OTHER PUBLICATIONS

Leica Microsystems Ltd.—"The Leica M841—The Ultimate Surgical Microscope System for Ophthalmology," Publication No. 10 M1 841 Oen, printed Jul. 2000 in Switzerland.
Medibell Medical Vision Technologies Ltd.—"Panoret 1000—Wide-Angle Digital Retinal Camera," printed at least as early as Oct. 2002.

* cited by examiner

*Primary Examiner*—Alicia M Harrington
(74) *Attorney, Agent, or Firm*—Hodgson Russ LLP

(57) ABSTRACT

The invention concerns a combined surgical microscope system having a surgical microscope and a retinal diagnostic device of modified configuration having transscleral pulsed illumination.

9 Claims, 3 Drawing Sheets

SURGICAL MICROSCOPE

CROSS REFERENCE TO RELATED APPLICATIONS

This application claims priority of the German patent application 103 02 401.8 which is incorporated by reference herein.

FIELD OF THE INVENTION

The invention concerns a surgical microscope having a beam path for a camera.

BACKGROUND OF THE INVENTION

With known surgical microscopes, for example with the M841 of the Leica company (see brochure, "The Leica M841—The Ultimate Surgical Microscope System for Ophthalmology," Publication no. 10 M1 841 Oen, printed VII.2000), surgery is performed on and below the retina (fundus) when ophthalmological diseases are present. The region extends from the macula to the ora serrata.

There also exist retinal diagnostic devices specifically for this sector, for example the retinal diagnostic device of Medibell Medical Vision Technologies Ltd., Haifa, Israel, referred to (in a brochure without publication information) as the "Panoret 1000—Wide-Angle Digital Retinal Camera." Retinal diagnostic devices in general are also commonly referred to as "retinal cameras" or "fundus cameras," and are produced by a number of manufacturers.

Retinal cameras are used for the diagnosis of corresponding diseases, and are sufficiently known.

The basic principle of such retinal cameras is that the observation beam path is guided through the patient's pupil together with the illuminating beam path.

Guidance of the observation and illumination beam paths together through the patient's pupil is, however, very difficult to implement. Compromises are therefore accepted.

The Medibell company developed the digital retinal camera indicated above, in which the observation beam was separated from the illumination beam so that these difficulties could thereby be circumvented. Observation is performed using a special optical system in direct contact with the patient's eye. Illumination is conveyed into the patient's eye in transscleral fashion (i.e. through the sclera of the eye) using a fiber illumination system.

The light source comprises three color diodes that are pulsed. The highresolution digital BW (black-and-white) camera is triggered simultaneously with the three colored light pulses. Image processing of the BW image yields an outstanding high-resolution color image on the color monitor or alternatively, given appropriate real-time processor performance, a live image. A similar arrangement, although not with pulsed color diodes but rather with a white-light source with color filter selection, is known from U.S. Pat. No. 6,309,070.

For a surgeon, it is desirable to use a retinal diagnostic device during an operation as well, i.e. not only for separate diagnosis. The reason is that utilization of the retinal diagnostic device is extremely cumbersome, since surgery using the surgical microscope must be interrupted in order to move the retinal diagnostic device over the patient's eye in order to make the desired (interim) diagnosis. The retinal diagnostic device must then, if applicable, be exchanged once again with the surgical microscope. Another desire on the part of ophthalmic surgeons is to receive from the diagnostic device not a separate, monoscopic image of the retina, but rather an enlargeable and, if applicable, stereoscopic one.

SUMMARY OF THE INVENTION

From these desires and from the disadvantages that presently exist, there arises the object upon which the invention is based, that of creating an improved surgical microscope that, while it is being used, permits the making of a diagnosis as in the case of a retinal diagnostic device, with no need to remove the surgical microscope from the operating position.

This object is achieved by a surgical microscope system generally comprising a surgical microscope having an observation beam path, a beam splitter arranged in the observation beam path, and a retinal diagnostic device having a digital retinal camera and a camera beam path from the beam splitter to the digital retinal camera.

The retinal diagnostic device preferably includes a retinal lens, a beam transposer, and an auxiliary lens movable into and out of the observation beam path, preferably under the control of a computer. In one embodiment, the computer also controls an illumination source and optical branching switch for selectively supplying light to the microscope or the retinal diagnostic device as needed.

Further embodiments of the invention are described herein.

BRIEF DESCRIPTION OF THE DRAWINGS

The invention will be explained in further detail, symbolically and by way of example, with reference to Figures. The Figures are described in continuous and overlapping fashion. Identical reference characters denote identical components, and reference characters having different indices indicate functionally identical or similar components. In the drawings.

DETAILED DESCRIPTION OF THE INVENTION

Figure 1:
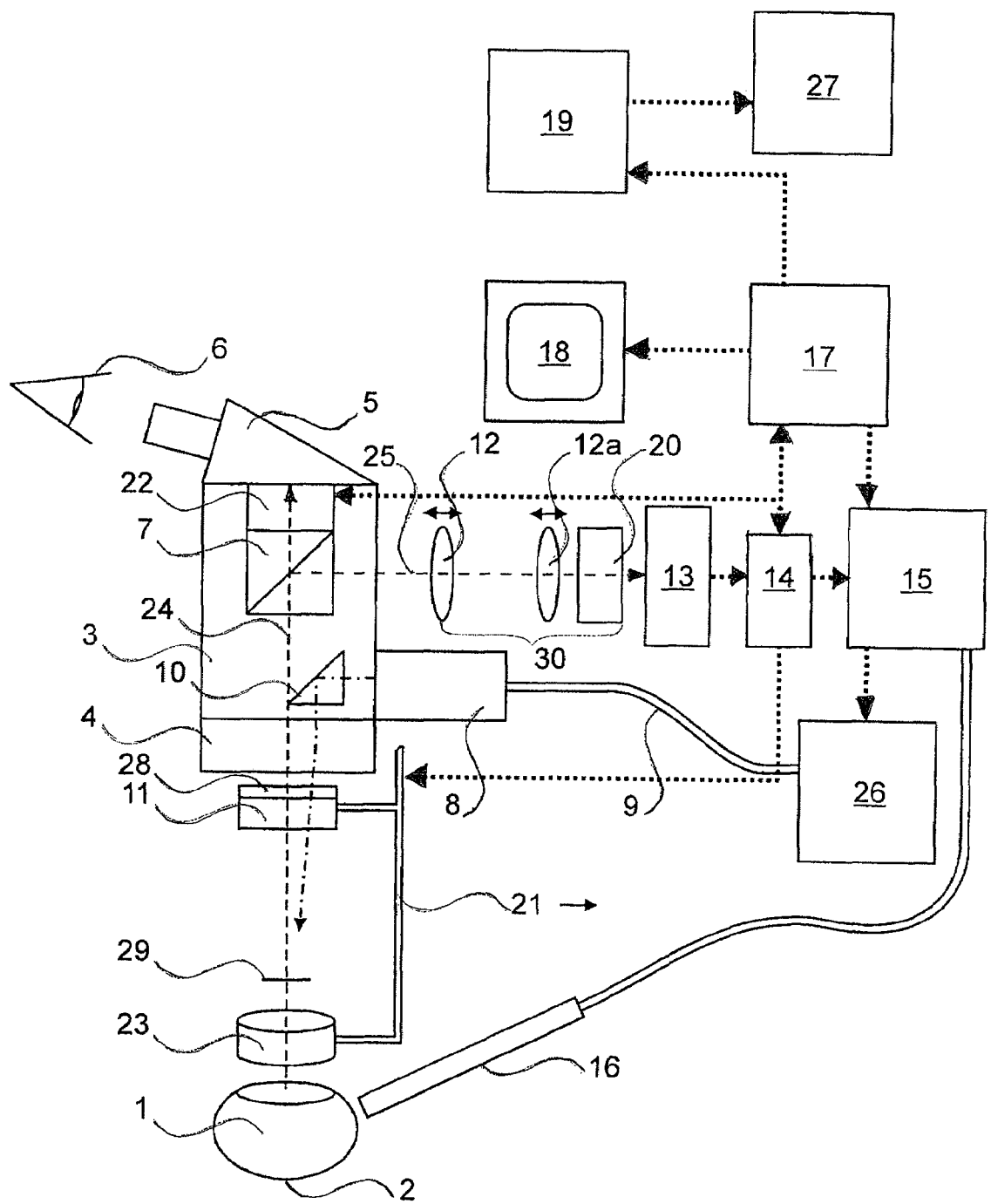
FIG. 1 shows the systematic configuration of a surgical microscope system in which, according to the present invention, a surgical microscope is combined with a retinal diagnostic device.

As is evident from FIG. 1, the inventive idea encompasses the fact that the retinal diagnostic device comprises a first component 13 and a second component 23. A surgical microscope 3 is incorporated between first component 13 and second component 23. In addition, a camera beam path 25 is coupled out of an observation beam path 24 by means of a beam splitter 7, as is usual, for example and in a manner known per se, for photographic or video documentation. After beam splitter 7, camera beam path 25 is directed through imaging lenses 12, 12a (lens groups can also be used instead of individual lenses) and through a deflection element 20 to a digital camera 13. Deflection element 20 that is depicted represents one possible optical deflection system and can comprise mirrors and/or prisms, and generates a rightreading and upright image on the image sensor of camera 13. The image sensor of camera 13 is typically an array of light sensitive pixels, for example a CCD array.

The imaging lenses or lens groups 12, 12a can selectably be displaced with respect to one another, so that the reproduction scale is variable and separate focusing is possible. The two lenses or lens groups 12, 12a form, together with deflection element 20, an imaging system 30 that alternatively can also comprise more than two lenses or lens groups 12, 12a, which alternatively can also be arranged in either fixed or axially movable fashion in camera beam path 25.

The electronic signals of the camera are conveyed via an image processing system 14 to a computer 17, and can be viewed as an image on a monitor 18, outputted in data output 19 as a printed image, or stored on known storage media, and can also be conveyed into a central document management system 27.

A stroboscopic light source 15 having at least two, in particular three color LEDs is triggered via computer 17 and camera 13 in such a way that light is radiated via a light guide 16 onto a patient's eye 1 only when an image is at that time being acquired with camera 13.

Surgical microscope 3, together with the retinal diagnostic device, constitutes a system which offers two application modes: an application mode as a surgical microscope, and an application mode as a retinal diagnostic device (fundus mode).

When the system is in fundus mode, a retina lens 23 together with a beam transposer 11 and an auxiliary lens 28, which are connected to surgical microscope 3 by means of a mechanical pivoting-in apparatus 21, are pivoted in front of a main objective 4. Beam transposer 11 transposes the left and right beam paths of surgical (stereo)microscope 3 in order to eliminate a pseudo-stereo effect that is caused by front-mounted retina lens 23. Beam transposer 11 can alternatively also be incorporated into surgical (stereo)microscope 3 at a different point 22. It is activated by computer 17 when the latter is switched into fundus mode. Auxiliary lens 28, with main objective 4, images at infinity the intermediate image 29 of fundus 2 generated by retina lens 23.

When the system is not in fundus mode, i.e. in the surgical (stereo)microscope application mode, retina lens 23, beam transposer 11, and auxiliary lens 28 are not pivoted in front of main objective 4. Patient's eye 1 is illuminated directly, via a deflection element 10 in surgical (stereo)microscope 3, by way of a microscope illumination system 8 that comprises a microscope light source 26 and a light-guiding cable 9.

Microscope light source 26 can advantageously be identical to camera light source 15, so that the patient's eye is also illuminated with the three-color LED stroboscopic light that minimizes retinal impact. It is preferable in this case if the flicker limit of observer's eye 6 is exceeded, so that a bright image impression is created but there is no need to direct too much-light energy into patient's eye 1.

A further inventive idea consists in the fact that optical adaptation of retinal camera 13 onto surgical microscope 3 is accomplished using a special imaging system 30. As mentioned, it comprises lenses or lens groups 12, 12a and deflection element 20. The inventor has recognized that it is sufficient if imaging system 30 is calculated and corrected specifically only for the wavelengths of the at least two color LEDs. A color correction such as that performed, for example, for visual observation in surgical microscope 3 is not necessary in this case. It is limited exclusively to the wavelengths offered by light source 15 and their discrete spectral distribution. According to the present invention, it is advantageously possible to use diffractive elements for chromatic correction here, in order to reduce the weight and overall length of imaging system 30.

In order to ensure optimum illumination of the pixels of the image sensor of camera 13, the beam profile after imaging system 30 in the light direction is calculated so that shadowing of the pixels by adjacent pixels does not occur, i.e. so that the bundle of rays strikes the surface of the image sensor's pixels almost perpendicularly. Advantageously, the resolution achieved by correction of the lens system need be no greater than that defined by the camera's pixel structure.

Since retina lens 23 and auxiliary lens 28, unlike imaging system 30, are also used visually by the surgeon, their optics are corrected in the conventional manner. Retina lens 23 can comprise a system that is in direct contact with the patient's eye, as is the case with the retinal camera of the Medibell company (U.S. Pat. No. 6,267,752); or known non-contact optical systems, e.g. of the Oculus company, can also be used.

Figure 2:
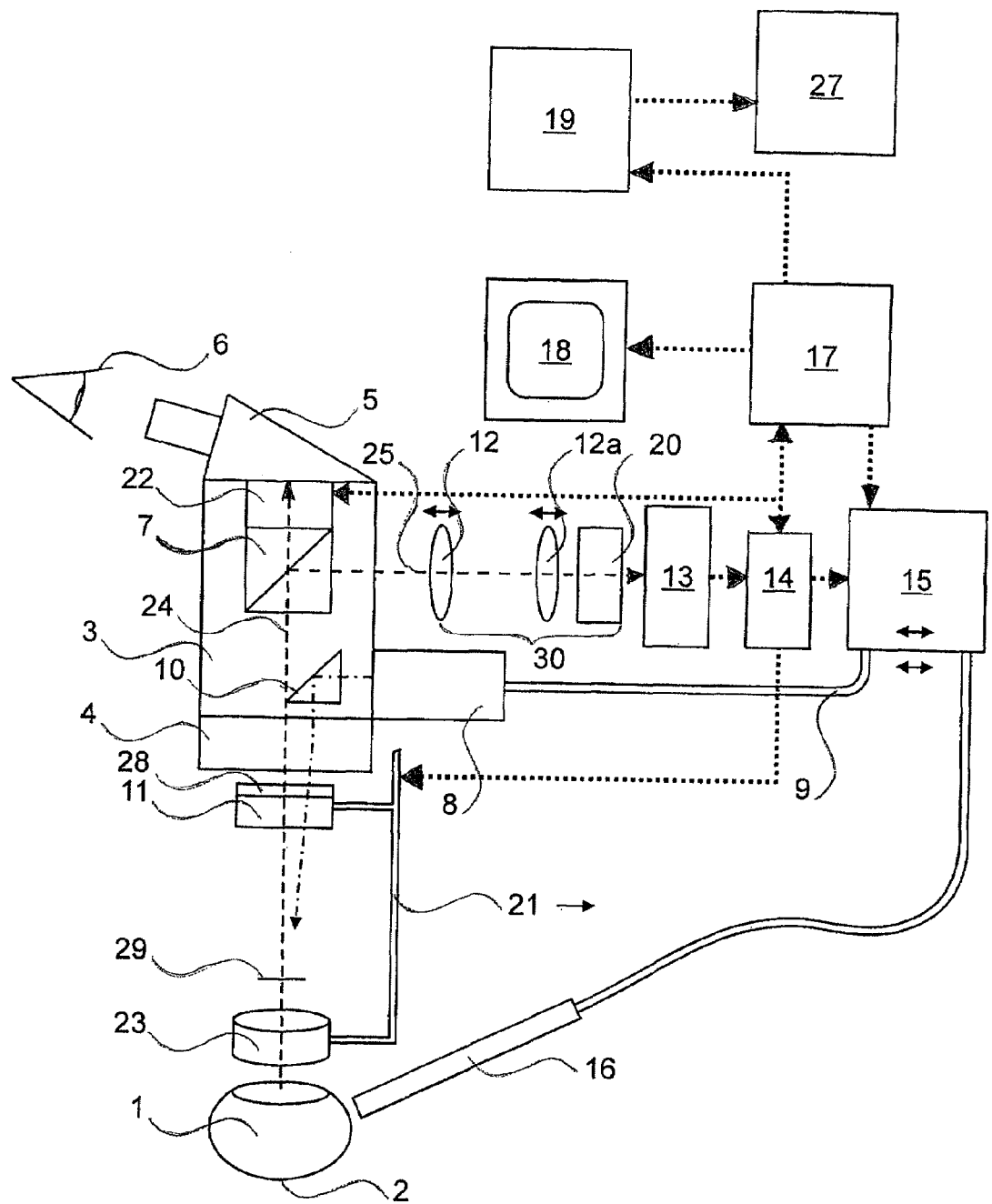
FIG. 2 shows a variant embodiment of the invention in which a common light source is provided and it is possible, based on a displacement of the light source and/or of the light guide, to switch the light feed to the respective light guide.

FIG. 2 shows a variant embodiment of a surgical microscope system according to the present invention having a surgical microscope 3 and an integrated retinal diagnostic device, in which a single light source 15 (e.g. a two- or three-color LED stroboscopic light) is provided both to feed light into light guide 9 for conventional illumination for surgical microscope 3, and to feed light into light guide 16 for transscleral illumination for the retinal diagnostic device. Simultaneous illumination through both light guides 9 and 16 is not provided for the retinal diagnostic device application mode (fundus mode), and is also difficult to implement, since the illumination supplied from light guide 9 for surgical microscope 3 would need to shine through the elements (auxiliary lens 28, beam transposer 11, and retina lens 23) pivoted in below main objective 4. Because of these optical elements that are arranged according to the present invention for operation of the retinal camera, simultaneous light feed to light guides 9 and 16 in fundus mode is not preferred. Accordingly, as schematically depicted, light guides 9 and 16 can be slid in front of light source 15, and/or light source 15 can be slid in front of light guide 9 and/or 16 that is required depending on the application mode selected (fundus mode or surgical microscope mode). This would mean the following arrangements according to the present invention for the two application modes:

In findus mode, light is fed only to light guide 16; microscope illumination system 8 does not supply any illumination, which would need to penetrate through the pivoted-in elements (auxiliary lens 28, beam transposer 11, and retina lens 23).

In surgical microscope mode, the optical elements comprising auxiliary lens 28, beam transposer 11, and retina lens 23 are not pivoted in front of main objective 4, and patient's eye 1 can thus be illuminated in conventional fashion through the pupil using microscope illumination system 8. In other words, light needs to be fed only to light guide 9. If simultaneous or exclusive transscleral illumination via light guide 16 is advantageous in this application mode, then according to the present invention the two illumination modes are intended to be combinable without restriction.

Figure 3:
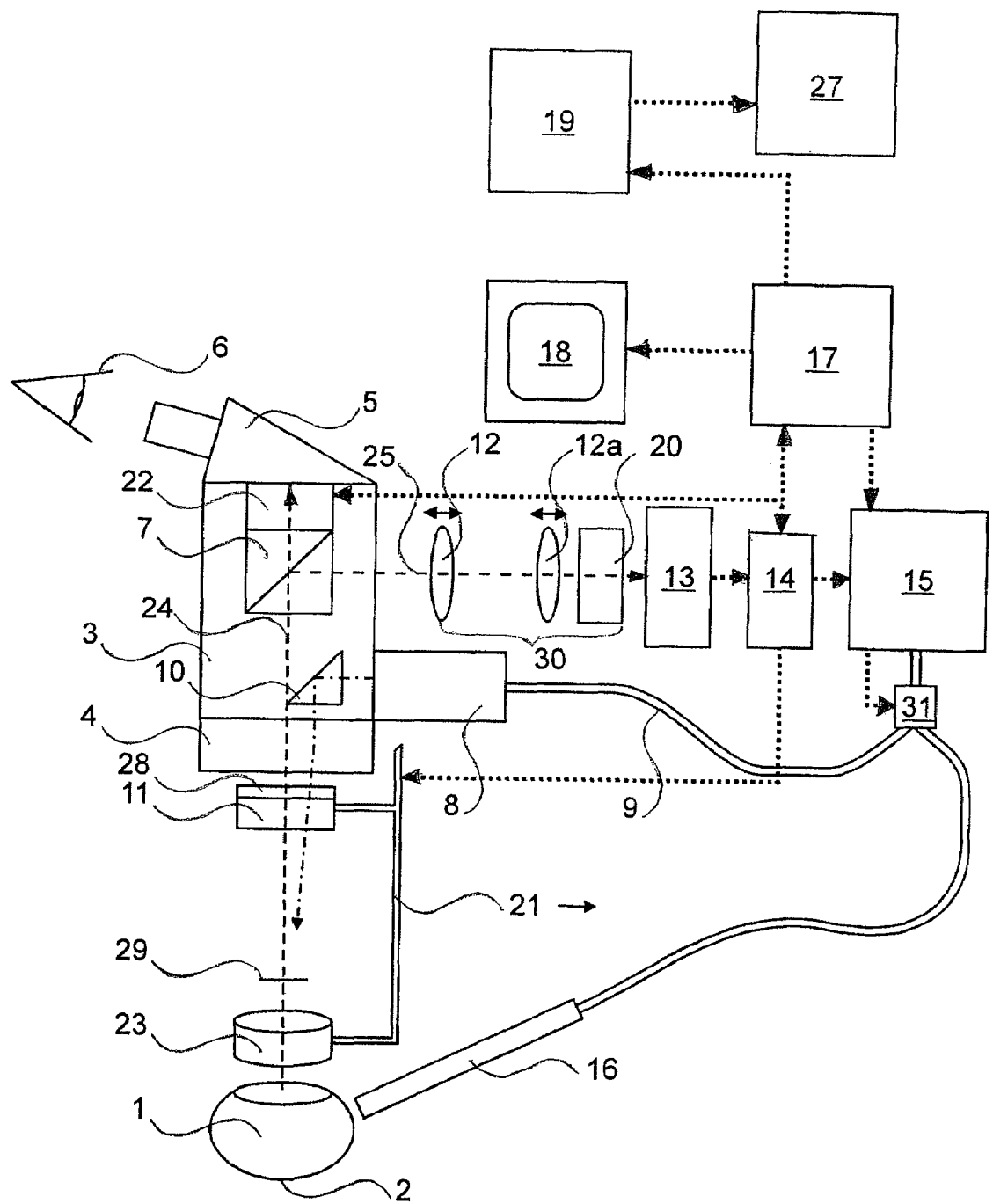
FIG. 3 shows a further variant embodiment of the invention in which a common light source and an optical light branching switch are provided.

FIG. 3 symbolically depicts the manner in which the requisite illumination can be switched by means of an optical light branching switch 31 controlled by computer 17.

PARTS LIST

1 Patient's eye
2 Retina (fundus)
3 Surgical microscope

4 Main objective
5 Stereo tube
6 Observer's eye
7 Beam splitter
8 Microscope illumination system
9 Light guide
10 Deflection element
11 Beam transposer
12, 12a Lens or lens group
13 Camera
14 Image processing system
15 Light source
16 Light guide
17 Computer
18 Monitor
19 Data output
20 Deflection element
21 Mechanical pivoting-in apparatus
22 Beam transposer (alternative installation location to 11)
23 Retina lens
24 Observation beam path
25 Coupled-out camera beam path
26 Microscope light source
27 Central document management system
28 Auxiliary lens
29 Intermediate image
30 Imaging system
31 Optical light branching switch

What is claimed is:

1. A surgical microscope system for observing an eye of a patient, the surgical microscope system comprising:
a surgical microscope having an observation beam path and a main objective in the observation beam path;
a beam splitter in the observation beam path;
a retinal diagnostic device having a digital retinal camera and a camera beam path separated from the observation beam path by the beam splitter, the camera beam path leading to the digital retinal camera, wherein the retinal diagnostic device includes a retinal lens in the observation beam path between the beam splitter and the patient's eye, the retinal lens being movable into and out of the observation beam path at a location between the main objective and the patient's eye; and
a beam transposer movable into and out of the observation beam path at a location between the main objective and the patient's eye.

2. The surgical microscope system as defined in claim 1, further comprising a pivoting-in apparatus carrying the retinal lens and the beam transposer, whereby the retinal lens and the beam transposer can be pivoted into and out of the observation beam path.

3. The surgical microscope system according to claim 1, further comprising an auxiliary lens movable into and out of the observation beam path at a location between the main objective and the patient's eye.

4. The surgical microscope system as defined in claim 3, further comprising a pivoting-in apparatus carrying the retinal lens, the beam transposer, and the auxiliary lens, whereby the retinal lens the beam transposer, and the auxiliary lens can be pivoted into and out of the observation beam path.

5. A surgical microscope system for observing an eye of a patient, the surgical microscope system comprising:
a surgical microscope having an observation beam path;
a beam splitter in the observation beam path;
a retinal diagnostic device having a digital retinal camera and a camera beam path separated from the observation beam path by the beam splitter, the camera beam path leading to the digital retinal camera;
a microscope illumination system associated with the surgical microscope;
a first light guide arranged to provide transscleral retinal illumination;
an illumination source connected to the microscope illumination system and to the first light guide to selectably provide illumination light to either of the microscope illumination system and the first light guide;
a second light guide arranged to deliver light to the microscope illumination system; and
an optical light branching switch connecting the first light guide and the second light guide to the illumination source, whereby light from the illumination source can be switched between the first light guide for use in transscleral retinal illumination and the second light guide for use in microscope illumination system.

6. The surgical microscope system as defined in claim 5, further comprising a computer connected to the optical light branching switch for controlling the optical light branching switch.

7. The surgical microscope system as defined in claim 6, wherein the surgical microscope includes a main objective in the observation beam path and the retinal diagnostic device includes a retinal lens, a beam transposer, and an auxiliary lens movable into and out of the observation beam path between the main objective and the patient's eye, wherein the retinal lens, the beam transposer, and the auxiliary lens are carried into and out of the observation beam path by a mechanism controlled by computer.

8. A surgical microscope system for observing an eye of a patient, the surgical microscope system comprising:
a surgical microscope having an observation beam path and a stereo tube on the observation beam path;
a beam splitter spaced from the stereo tube in the observation beam path
a retinal diagnostic device having a digital retinal camera and a camera beam path from the beam splitter to the digital retinal camera, the retinal diagnostic device further having a beam transposer removably installed in the observation beam path between the stereo tube and the beam splitter.

9. The surgical microscope system as defined in claim 8, wherein further comprising a computer for controlling installation of the transposer in the observation beam path.

* * * * *